United States Patent
Becker et al.

(10) Patent No.: US 11,413,003 B2
(45) Date of Patent: Aug. 16, 2022

(54) SETTING AN X-RAY EMISSION UNIT

(71) Applicants: Anne-Katrin Becker, Nuremberg (DE); Georg Buchheim, Forchheim (DE); Frank Dennerlein, Forchheim (DE); Franziska Dinse, Heiligenstadt (DE); Philip Hafner, Zirndorf (DE); Sultan Haider, Erlangen (DE); Clemens Jörger, Forchheim (DE)

(72) Inventors: Anne-Katrin Becker, Nuremberg (DE); Georg Buchheim, Forchheim (DE); Frank Dennerlein, Forchheim (DE); Franziska Dinse, Heiligenstadt (DE); Philip Hafner, Zirndorf (DE); Sultan Haider, Erlangen (DE); Clemens Jörger, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 147 days.

(21) Appl. No.: 15/121,721

(22) PCT Filed: Jan. 13, 2015

(86) PCT No.: PCT/EP2015/050451
§ 371 (c)(1),
(2) Date: Aug. 25, 2016

(87) PCT Pub. No.: WO2015/128108
PCT Pub. Date: Sep. 3, 2015

(65) Prior Publication Data
US 2016/0374639 A1    Dec. 29, 2016

(30) Foreign Application Priority Data
Feb. 26, 2014  (DE) .......................... 102014203492.2

(51) Int. Cl.
*A61B 6/00*  (2006.01)
*A61B 6/08*  (2006.01)

(52) U.S. Cl.
CPC ................ *A61B 6/547* (2013.01); *A61B 6/08* (2013.01); *A61B 6/4464* (2013.01); *A61B 6/545* (2013.01)

(58) Field of Classification Search
None
See application file for complete search history.

(56) References Cited

U.S. PATENT DOCUMENTS 4,896,343 A    1/1990  Saunders
5,848,126 A *  12/1998 Fujita .................... A61B 6/032
                                                    378/195

(Continued)

FOREIGN PATENT DOCUMENTS

CN    101023890 A     8/2007
DE    102004042790 A1  3/2006

(Continued)

OTHER PUBLICATIONS

German Office Action for German Application No. 10 2014 203 492.2, dated Oct. 9, 2014, in English.

(Continued)

*Primary Examiner* — Hoon K Song
(74) *Attorney, Agent, or Firm* — Lempia Summerfield Katz LLC

(57) ABSTRACT

Setting an x-ray emission unit includes acquiring image data with the aid of a number of image recording units. A body region to be recorded of an examination object is identified based on the image data. Position data of the body region to be recorded is established, and the x-ray emission unit is set using the position data.

15 Claims, 2 Drawing Sheets

(56) References Cited

U.S. PATENT DOCUMENTS

| | | | |
|---|---|---|---|
| 6,267,503 B1 | 7/2001 | McBride | |
| 7,436,927 B2 | 10/2008 | Hempel | |
| 7,720,198 B2 | 5/2010 | Schliermann | |
| 2004/0081341 A1* | 4/2004 | Cherek | A61B 6/469 382/128 |
| 2007/0172102 A1 | 7/2007 | Hempel | |
| 2008/0101538 A1 | 5/2008 | Schliermann | |
| 2011/0164728 A1 | 7/2011 | Tsuchiya et al. | |
| 2013/0083894 A1* | 4/2013 | Niebler | A61B 6/4441 378/62 |
| 2013/0343523 A1* | 12/2013 | Lee | A61B 6/545 378/63 |
| 2015/0117601 A1* | 4/2015 | Keeve | A61B 6/5241 378/41 |
| 2018/0360401 A1* | 12/2018 | Lee | A61B 5/1128 |

FOREIGN PATENT DOCUMENTS

| | | |
|---|---|---|
| DE | 102006001850 A1 | 8/2007 |
| DE | 69737604 T2 | 12/2007 |
| DE | 102012201798 A1 | 8/2013 |
| DE | 102012008812 A1 | 10/2013 |
| WO | WO2010044168 A1 | 4/2010 |

OTHER PUBLICATIONS

PCT International Search Report for corresponding PCT/EP2015/050451, dated Mar. 30, 2015.
Chinese Office Action for Chinese Application No. 201580010753.3 dated Aug. 2, 2018.

* cited by examiner

SETTING AN X-RAY EMISSION UNIT

This application is the National Stage of International Application No. PCT/EP2015/050451, filed Jan. 13, 2015, which claims the benefit of German Patent Application No. 10 2014 203 492.2, filed Feb. 26, 2014. The entire contents of these documents are hereby incorporated herein by reference.

BACKGROUND

The present embodiments relate to setting an x-ray emission unit using image data.

Several methods are already known for setting medical diagnostic instruments. Without neglecting care and quality, the examination time is to be kept short. This is because important resources such as staff, examination rooms, and examination instruments are tied up during the examination, and this would otherwise lead to an increase in the treatment costs. The x-ray radiation exposure of the patient is to be kept as low as possible by way of advantageous settings.

In the case of a computed tomography scanner with a method for positioning the patient within the gantry of the computed tomography scanner as known from practice, an image recording instrument detects a marking previously applied to the patient and localizes the marking by the image processing. As a result, a spatial correlation may be established between the detected position of the patient and the coordinate system of the computed tomography scanner, with the patient couch of the computed tomography scanner subsequently being displaced automatically into a desired examination position. A problem hereby is that a marking is to initially be applied to the patient by the treating medical practitioner or appropriately trained medical staff. Attaching such markings to the patient may be undesirable for various reasons, and this method and the device adapted thereto are thus not suitable in all situations.

Practice has disclosed the case where, as an alternative to the above-described positioning device and the positioning method, the patient may be aligned by a light or laser sight. The specification of the length of the scanning range is represented by appropriate light markings such that the staff undertakes the appropriate setting of the scan region directly at the patient.

In the aforementioned cases, a manual, time-consuming and hardly satisfactory interaction by the operating staff is to be provided, which may be disadvantageous, particularly in the case of mass screenings. If topogram recordings are also produced in addition to the more precise positioning, there is an increased radiation exposure of the patient.

A further method allows automatic determination of the individual body regions by carrying out an image analysis, known per se, of a recording of a patient on a patient couch of a computed tomography scanner. In this case, the image of a patient on the couch is automatically analyzed, and there is automatic acquisition of the individual body regions based on typical features in the image. Following this, individual scan regions may be determined, whereupon the patient is positioned in the computed tomography scanner with the aid of the adjustable patient couch.

However, the aforementioned methods assume that the patient is repositioned on an adjustable patient couch for the purposes of being positioned, which may be difficult for the staff and uncomfortable for the patient. This requires additional time. Further parameters that are relevant to the examination and dependent on the patient are to be entered into the diagnostic instruments in each method.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an alternative, more comfortable method and a corresponding x-ray system with an x-ray emission unit, by which the above-described disadvantages are reduced or completely avoided, are provided.

In the method for setting an x-ray emission unit, image data is initially acquired with the aid of a number of image recording units. A body region to be recorded of an examination object is identified based on this image data, and position data of the body region to be recorded is subsequently established. The x-ray emission unit is set using precisely this position data.

Therefore, one or more of the present embodiments depart from the prior art, in which the patient is positioned in, or in relation to, the stationary diagnostic instrument with the aid of a movable couch. By contrast, the method according to one or more of the present embodiments uses the position data obtained from the image data in order to undertake settings of the x-ray emission unit.

The x-ray emission unit denotes the radiation head or the x-ray head of a typical x-ray instrument. Situated therein is, inter alia, an x-ray emission source that serves to x-ray the examination object. The examination object may be a human or animal patient, of whom x-ray data is intended to be recorded for diagnostic purposes.

Setting an x-ray emission unit includes a number of parameters that are accounted for in one or more of the present embodiments. Position data is calculated for establishing these parameters for the examination. The position data includes both the position of the patient and organs of the patient, and the relative coordinates and angles of the x-ray emission unit in relation to the patient. Image data that is recorded by image recording units and automatically evaluated by suitable ways, such as, for example, an image processing program executed on a computer unit, are used as a basis for the calculation. Body regions or organs are identified on account of specific features, and, for example, the regions to be examined are thus identified and determined as a basis for the parameter calculation. This determination may be carried out by selecting and entering an examination region at a computer unit, an organ program selected in advance (e.g., an organ-specific control protocol), and/or via data that was transmitted in advance by a radiology information system (RIS). The aforementioned image recording units are cameras or sensors that operate in the visible light range and/or in the vicinity of the visible (e.g., infrared) light range (e.g., explicitly do not generate x-ray images). The image recording units may be installed in a movable and/or stationary manner in the room.

Thus, in contrast to the prior art, it is not the patient who is positioned, but position data established from the image data is used to set the x-ray emission unit. This is advantageous in that the patient need not be repositioned on a suitable, movable couch, which requires effort, time and possibly pain from staff and patient. This is because the setting method according to one or more of the present embodiments renders possible an examination even in different positions of the patient, such as, for example, sitting, standing, or lying.

An x-ray system set forth at the outset includes an x-ray emission unit that is connected to a device for automatically positioning the x-ray emission unit in the room. The x-ray system includes a number of image recording units that are embodied to acquire image data. Additionally, the x-ray system includes a control unit connected to the x-ray emission unit and the image recording units. The control unit is embodied for identifying a number of body regions of an examination object to be recorded based on the image data. The control unit is also embodied to establish position data of the body regions to be recorded and to set the x-ray emission unit using precisely this position data.

X-ray emission units are often fastened in a space-saving manner with arms and joints on a ceiling such that the arms and joints are positionable in relation to the patient. In one embodiment, such a ceiling-mounted x-ray emission unit is used within the scope of the present embodiments. Thus, the x-ray emission unit may be automatically positioned in the room via one embodiment of an x-ray system, inter alia, based on the position data (e.g., depending on the region to be examined, the x-ray emission unit is displaced or rotated into a suitable examination position with the aid of drive elements).

The image data is evaluated in the control unit. The identified body regions may be depicted in a highlighted manner in an image of the patient on a monitor connected to the control unit for the purposes of selection. The highlighting may be clarified by hatching, contour, or color. The selection of a region to be examined is now carried out, for example, via clicking on the appropriate position of the patient image, by selecting a specific organ program, or by using patient data known from the RIS.

The x-ray emission unit set forth at the outset for an x-ray system according to one or more of the present embodiments includes an image recording unit (e.g., a camera). In other words, this image recording unit is moved together with the x-ray emission unit and may have a view axis that extends substantially in the direction of the emitted x-rays. The image recording unit may also be integrated directly into a housing of the x-ray emission unit. Alternatively, an external attachment to the housing may be provided.

An advantage of this arrangement is that only one image recording unit is thus used for recording image data of the patient from different viewing angles. Hence, dead angles are avoided with only one image recording unit in the case of sufficient positionability of the x-ray emission unit, and a recording that is as comprehensive as possible is achieved, ultimately leading to a better configuration of the x-ray emission unit.

In one embodiment, the x-ray emission unit may be aligned "by remote control" and in relation to the patient as a result of the directly transferred image from the camera. An image recording unit attached to the x-ray emission unit may easily be retrofitted into an existing x-ray system, and existing x-ray systems may thus be reconfigured to form x-ray systems according to one or more of the present embodiments in a cost-effective manner.

A majority of the aforementioned acts of the method for setting an x-ray emission unit (e.g., identifying the body regions to be recorded and establishing position data) may be realized completely or in part in the form of software modules in a processor of a corresponding control apparatus. This is advantageous to the extent that an already available control apparatus may also be retrofitted for carrying out the method according to one or more of the present embodiments via a software installation. The present embodiments therefore also include a computer program (e.g., stored in a non-transitory computer-readable storage medium) that is directly loadable in a processor of a programmable control apparatus of an x-ray system, including program code (e.g., instructions) for executing all acts of the method when the program is executed in the control apparatus.

The x-ray system according to one or more of the present embodiments or the x-ray emission unit according to one or more of the present embodiments may also be developed in a manner analogous to the method.

In the case of an exemplary embodiment of the method, setting the x-ray emission unit includes automatic positioning of the x-ray emission unit in addition to the subsequently mentioned further setting options. As a result of this motor-driven alignment, the movable x-ray emission unit may be brought into a more exact radiation or examination position than would be possible by way of the operating staff. This advantageously is accompanied by a better reproducibility of the examination results. In one embodiment, positioning of the x-ray emission unit in all three spatial directions and, for example, also about all three axes of rotation may be provided.

In a further variant, automatic positioning may also take place in two stages (e.g., relatively approximate pre-positioning, followed by fine positioning).

In one embodiment, the x-ray emission unit according to one or more of the present embodiments includes a laser sight that projects a number of contour lines (e.g., at least one contour line) onto the examination object. Three-dimensional scanning data of the examination object is acquired by the image recording units while there is movement of the contour line(s). The contour line may be moved by adjusting the laser sight or by rotating or displacing the entire x-ray emission unit. Thus, the laser line that was straight at the outset changes the form thereof as a contour line on the patient during the movement thereof (e.g., during the scanning process). The line is recorded as successive image data (e.g., as scanning data). Thereupon, a three-dimensional contour of at least part of the patient (referred to as "model" of the patient below) is created incrementally from this three-dimensional point cloud with the aid of a suitable reconstruction method.

The position data for the organs may be determined more exactly from this model than from simple, two-dimensional image data records. Thus, negative influences of truncations may be avoided, particularly in the case of 3D reconstructions of organs from the x-ray data, since the overall volume is already known from the laser scan.

Thus, the identification of the body regions to be recorded may take place based on this model in the method according to one or more of the present embodiments (e.g., using an image of the examination object generated from the three-dimensional scanning data). The acquired body regions may be observed much more vividly and selected more comfortably for the examination in this three-dimensional image, which is possibly even rotatable and/or capable of magnification.

The contour data and/or the model acquired with the aid of the laser sight may, for example, be used within the aforementioned fine positioning.

Further parameters for setting the x-ray emission unit are established alternatively (e.g., if the x-ray emission unit is already correctly positioned in the specific case) or also based on the image data and/or three-dimensional scanning data in the case of an exemplary embodiment. In one embodiment, apart from the positioning, other settings are also undertaken on the x-ray emission unit, such as, for example, the dose regulation, corrected generator values, and/or the collimation area. Additionally, the water equivalent (e.g., for fluoroscopic examinations) may thus be established. As a result, a good image without "settling" of the controller for determining the water equivalent for the dose adjustment may be provided prior to the beginning of the examination since the patient volume in the examination region is already known. This advantageously leads to a lower radiation exposure of the patient.

For example, parameters such as the dose or the collimation may also be adapted in an automated manner based on the contour data acquired with the aid of the laser sight and/or based on the model. Thus, for example, information about the thickness of the patient in the region of interest may already be established with the aid of a contour line, and the ideal dose may also be determined therefrom.

In one embodiment, a check is carried out in the method according to one or more of the present embodiments after carrying out the setting as to whether the examination object is changing a position and, where necessary, a change in the setting is undertaken and/or a warning signal is output. Since recording of the image data may continue during the entire examination duration, a change in position of the patient may be determined at all times in situ using an initial image as a reference. If a tolerance range defined in advance is exceeded, an automatic correction of the x-ray system may attempt to continue to provide the success of the examination, and/or an acoustic and/or optical signal may be generated to warn the staff.

A first adjustment, in which the x-ray emission unit is aligned onto the examination object, is carried out in an exemplary embodiment of the method prior to acquiring the image data. This approximate adjustment may optionally be carried out based on the image data of the image recording units attached in the room, or the approximate adjustment may take place using the parameters that are set in an organ program selected at the start of the examination. The approximate alignment may also be undertaken manually by the staff at the outset. This approximate adjustment reduces the scanning time since the x-ray emission apparatus (e.g., the laser sight as well) is already approximately aligned onto the region to be examined, and a whole body scan for identification is no longer required.

At least some of the acts of the method according to one or more of the present embodiments are carried out using an organ-specific control protocol in an exemplary embodiment. This control protocol (e.g., an organ program) is a fully programmed control program for automatic control of the diagnostic instrument). In general, a plurality of different organ programs are stored in the memory of the control apparatus of the instrument, which an operator may select and, optionally, modify, depending on the examination object. The control parameters include parameters that, for example, take into account the position and the approximate volume of the organ and, to this end, predetermine, for example, the position and extent of an image to be produced, the aperture to be used, a dose to be set, etc. By a preceding selection of an organ program, the acts of the method to which the control parameters are applied may be shortened since benchmarks are already known for some of the parameters relevant to the examination.

In one embodiment, the x-ray emission unit of the x-ray system includes a laser sight, and the laser sight is embodied for three-dimensional scanning of the examination object.

In each of the automated processes carried out within the scope of the present embodiments, a preceding display may also be provided at a user interface, and a further act only occurs after receiving a confirmation signal or change signal to be entered by the user. By way of example, an automatically selected body region may initially be marked directly on the patient (e.g., with the aid of the laser beams) or the automatically selected body region may be marked on any display instrument in a representation of the patient (e.g., live image or model).

BRIEF DESCRIPTION OF THE DRAWINGS

Same components are provided with same reference signs in the various figures. As a rule, the figures are not to scale.

DETAILED DESCRIPTION

Figure 1:
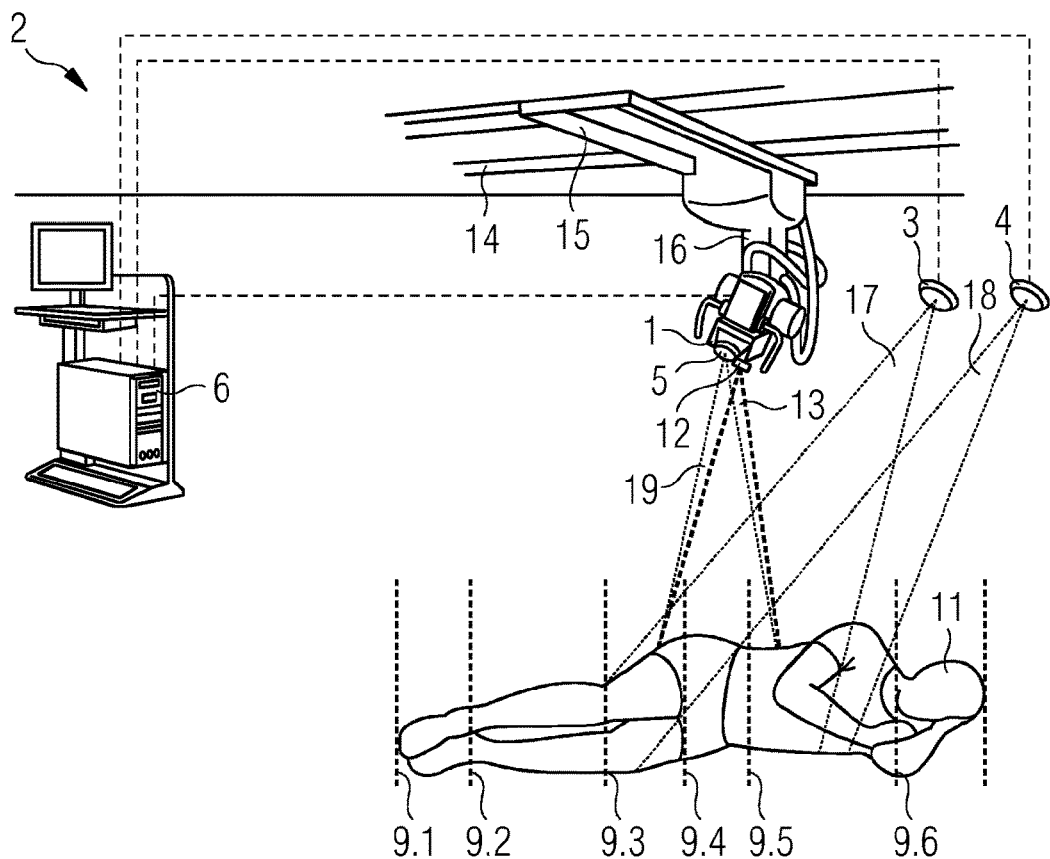
FIG. 1 shows a schematic illustration of an exemplary embodiment of an x-ray system.

FIG. 1 shows an exemplary embodiment of an x-ray system 2. A human patient is depicted in an exemplary manner as an examination object 11. For reasons of simplicity, the illustration of an examination room is dispensed with; however, the examination room serves for the attachment of parts of the x-ray system. The patient 11 is situated in a lying position under an x-ray emission unit 1 with ceiling stand 14, 15, 16 (e.g., a positioner). The ceiling stand 14, 15, 16 in this case includes two pairs of parallel rails 14, 15 that are orthogonal to one another and an articulated arm 16, on which the x-ray emission unit 1 is attached in a movable manner on the ceiling of the room. An image recording unit 5 with a viewing angle 19 is fastened laterally to the housing of the x-ray emission unit 1. The viewing angle includes the x-ray emission direction of the x-ray emission unit 1. A laser target sight 12 is attached directly under the x-ray emission unit 1. The laser target sight 12 emits a laser line 13. Further image recording units 3, 4 are fastened in the room with different viewing angles 17 and 18, respectively.

The following body regions are marked on the patient 11: feet 9.1, lower leg 9.2, thigh 9.3, hip/abdomen 9.4, upper body 9.5 and head 9.6. In terms of spatial arrangement thereof, a control unit 6 (e.g., a controller) is independent of the remaining parts of the x-ray system 2 but connected to the image recording units 3, 4, 5, the x-ray emission unit 1 and, via the x-ray emission unit 1, the positioner 14, 15, 16.

Image data DAT of the patient 11 is detected with the aid of the image recording units 3, 4, 5, as is explained in more detail below based on FIG. 4, and transferred to the control unit 6, which is depicted as a computer in FIG. 1. In the computer, the body regions 9.1, 9.2, 9.3, 9.4, 9.5, 9.6 of the patient 11 are identified, regions to be examined are selected, and the position data thereof and the position data of the x-ray emission unit are established. Using the position data POS, which also includes the volumes of the organs to be examined, the x-ray emission unit is aligned in relation to the patient for the examination, and further parameters PAR such as the radiation dose and/or collimation area are set in order to obtain x-ray data that is as precise as possible for the diagnosis.

Even though three image recording units are depicted in FIG. 1, more or fewer thereof may be used without departing from the scope of the invention. Independently of the illustration, the method according to one or more of the present embodiments and the x-ray system may be used to examine the patient in a seated or standing position. The laser sight attached at the bottom of the housing of the x-ray emission apparatus 1 in FIG. 1 may likewise be installed directly into the housing of the x-ray emission apparatus. In one embodiment, a scan is carried out with this laser sight in order to acquire the image data DAT. The scan is explained in more detail based on FIGS. 2 and 3. However, if no three-dimensional scan data is present, parameters POS/PAR for setting the x-ray emission unit may also be established from the other image data DAT.

Figure 2:
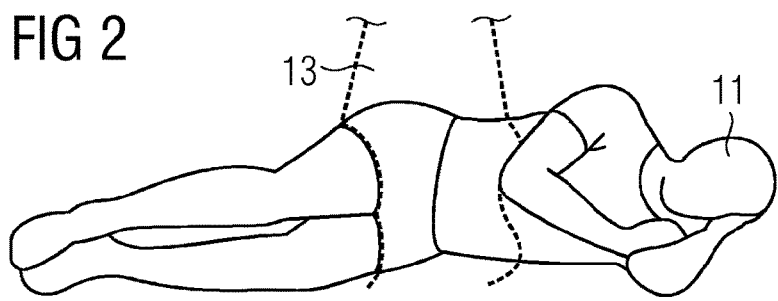
FIG. 2 shows an exemplary magnification of a region from FIG. 1 illuminated by a laser sight.

FIG. 2 shows a magnified section from FIG. 1. The hip region 9.4 of the patient 11, which is illuminated by the laser line 13 emitted by the laser sight 12, is depicted. The laser line may be moved by displacing and/or rotating the x-ray emission unit 1 or adjusting the laser sight such that the whole patient is scanned step-by-step. A plurality of laser lines (e.g., two lines crossing perpendicular to one another) may be generated at the same time via a laser sight and used for the scanning.

Figure 3:
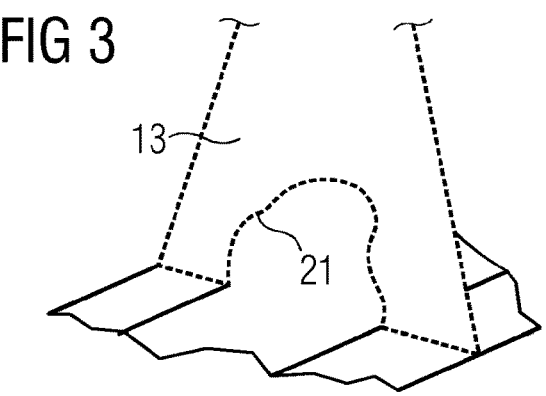
FIG. 3 shows a sectional view of the region from FIG. 2 illuminated by the laser sight.

FIG. 3 shows a sectional view through the patient 11 in the same body region as in FIG. 2. The laser line 13 is incident on the body surface of the patient, and the laser line 13 is detected at the body surface of the patient as a contour line 21 by the image recording units. As described above, the patient may be scanned in bit-by-bit. With the aid of this scanning data, a three-dimensional model of the patient may be created, with the settings for the x-ray emission unit then being established in the control unit while the model is used.

Figure 4:
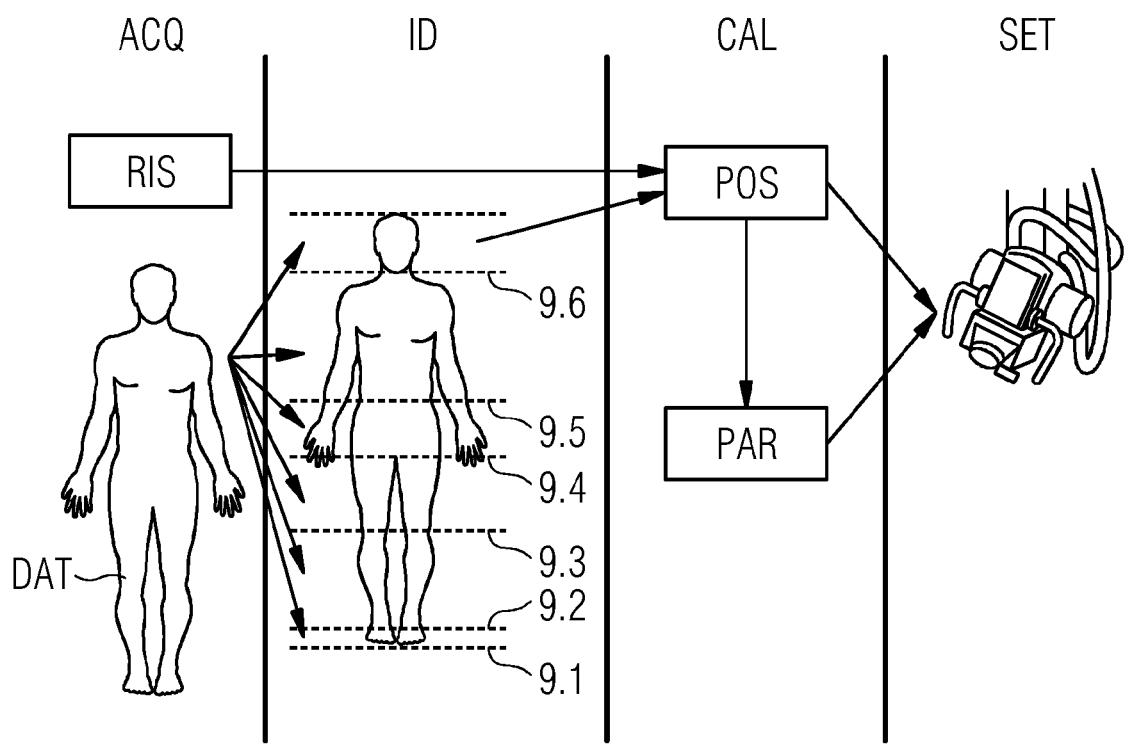
FIG. 4 shows a flowchart of an exemplary embodiment of the method.

FIG. 4 shows a flowchart of an exemplary embodiment of a method according to one or more of the present embodiments. The method is divided into four acts: acquisition ACQ, identification ID, establishment CAL, and setting SET. The image data DAT of the patient is acquired in act ACQ. In the next act ID, an image evaluation program identifies individual body regions 9.1, 9.2, 9.3, 9.4, 9.5, 9.6 from this data, whereupon the regions to be examined are determined, possibly using further data RIS from the radiology information system. Based on this, position data POS is established in the act CAL, which follows. The position data also includes the position data of the x-ray emission unit in addition to the position data of the body regions to be examined. From this, an optimized position and further parameters PAR for the x-ray emission unit are determined. The x-ray emission unit is set according to these prescriptions in the last act of the method SET.

Therefore, the method according to one or more of the present embodiments simplifies the setting of an x-ray emission unit since many inputs that require specialist knowledge in the art are carried out automatically. As a result, the diagnostic results are additionally reproducible to a greater extent. As a result of the three-dimensional modeling of the patient, the method makes the operation more comfortable, and ultimately, the examination time may be reduced further by using organ programs, which results in a lower exposure of the patient and better use of the resources.

The method described in detail above and the depicted x-ray system are merely exemplary embodiments that may be modified by a person skilled in the art in a greatly varying manner without departing from the scope of the invention. The use of the indefinite article "a" or "an" does not preclude the relevant features from also being present a number of times. The terms "unit" and "system" do not preclude the relevant components from including a plurality of interacting subcomponents, which may optionally also be distributed in space.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for setting an x-ray emission unit positionable in three spatial directions and three axes of rotation for imaging an organ, the method comprising:
   identifying a control protocol of a plurality of control protocols stored in a memory, the identified control protocol being specific to the organ and being a fully programmed control program that sets parameters that predetermine a position and an extent of an image to be produced; and
   in response to the identifying of the control protocol:
   acquiring image data with the aid of a number of image recording units;
   creating a three-dimensional model of the patient based on the image data;
   identifying a body region to be recorded of an examination object based on the three-dimensional model and the organ specific to the identified control protocol;
   calculating position data of the body region to be recorded, the position data including a location of the organ; and
   setting the x-ray emission unit using the position data including the location of the organ,
   wherein setting the x-ray emission unit comprises automatic positioning of the x-ray emission unit in the three spatial directions and the three axes of rotation, and automatic setting of an aperture to be used, a dose to be set, or a combination thereof based on the identified control protocol as adapted by the three-dimensional model.

2. The method of claim 1, wherein the x-ray emission unit comprises a laser sight that projects a number of contour lines onto the examination object, and
   wherein three-dimensional scanning data of the examination object is acquired by the image recording units while the contour lines are moved.

3. The method of claim 2, wherein the identifying of the body regions to be recorded comprises identifying the body regions to be recorded using an image of the examination object produced from the three-dimensional scanning data.

4. The method of claim 2, further comprising establishing further parameters for setting the x-ray emission unit based on the image data, the three-dimensional scanning data, or a combination thereof.

5. The method of claim 1, further comprising carrying out a check after carrying out a setting as to whether the examination object is changing a position, changing the setting, outputting a warning signal, or any combination thereof.

6. The method of claim 1, further comprising carrying out a first adjustment, in which the x-ray emission unit is aligned onto the examination object, prior to acquiring the image data.

7. An x-ray system comprising:
an x-ray emission unit positionable in three spatial directions and three axes of rotation for imaging an organ and connected to a device that automatically positions the x-ray emission unit in a room;
a number of image recording units configured to acquire image data; and
a controller connected to the x-ray emission unit and the image recording units and configured to identify a control protocol of a plurality of control protocols stored in a memory, the identified control protocol being specific to the organ and being a fully programmed control program that sets parameters that predetermine a position and an extent of an image to be produced, create, in response to the identification of the control protocol, a three-dimensional model of the patient based on the image data, identify, in response to the identification of the control protocol, a number of body regions to be recorded of an examination object based on the three-dimensional model and the organ specific to the identified control protocol, establish, in response to the identification of the control protocol, position data of the body regions to be recorded, the position data including a location of the organ, automatically position, in response to the identification of the control protocol, the x-ray emission unit in the three spatial directions and the three axes of rotation using the position data including the location of the organ, and automatically set of an aperture to be used, a dose to be set, or a combination thereof based on the identified control protocol as adapted by the three-dimensional model.

8. The x-ray system of claim 7, wherein the x-ray emission unit comprises a laser sight and is configured for three-dimensional scanning of the examination object.

9. An x-ray emission unit for an x-ray system, the x-ray system comprising a number of image recording units configured to acquire image data, a controller connected to the x-ray emission unit and the image recording units and configured to identify a control protocol of a plurality of control protocols stored in a memory, the identified control protocol being specific to the organ and being a fully programmed control program that sets parameters that predetermine a position and an extent of an image to be produced, create, in response to the identification of the control protocol, a three-dimensional model of the patient based on the image data, identify, in response to the identification of the control protocol, a number of body regions to be recorded of an examination object based on the three-dimensional model and the organ specific to the identified control protocol, establish, in response to the identification of the control protocol, position data of the body regions to be recorded, the position data including a location of an organ, automatically position, in response to the identification of the control protocol, the x-ray emission unit in the three spatial directions and the three axes of rotation using the position data including the location of the organ, and automatically set of an aperture to be used, a dose to be set, or a combination thereof based on the identified control protocol as adapted by the three-dimensional model, the x-ray emission unit comprising:
an x-ray emission unit positionable in three spatial directions and three axes of rotation configured to image and connected to a device that automatically positions the x-ray emission unit in a room; and
an image recording unit of the number of image recording units.

10. A computer program product comprising a non-transitory computer-readable storage medium having program code that is directly loadable into a processor of a programmable controller of an x-ray system for imaging an organ, the program code being executable by the processor to:
identify a control protocol of a plurality of control protocols stored in a memory, the identified control protocol being specific to the organ and being a fully programmed control program that sets parameters that predetermine a position and an extent of an image to be produced; and
in response to the identification of the control protocol:
acquire image data with the aid of a number of image recording units;
create a three-dimensional model of the patient based on the image data;
identify a body region to be recorded of an examination object based on the three-dimensional model and the organ specific to the identified control protocol;
calculate position data of the body region to be recorded, the position data including a location of the organ;
set an x-ray emission unit positionable in three spatial directions and three axes of rotation using the position data including the location of the organ,
wherein the set of the x-ray emission units comprises automatic position of the x-ray emission unit in the three spatial directions and the three axes of rotation, and automatic set of an aperture to be used, a dose to be set, or a combination thereof based on the identified control protocol as adapted by the three-dimensional model.

11. The x-ray system of claim 8, wherein the laser sight projects a number of contour lines onto the examination object, and
wherein three-dimensional scanning data of the examination object is acquired by the image recording units while the contour lines are moved.

12. The x-ray system of claim 11, wherein the identification of the body regions to be recorded comprises identification of the body regions to be recorded using an image of the examination object produced from the three-dimensional scanning data.

13. The x-ray system of claim 11, wherein the controller is further configured to establish further parameters for setting the x-ray emission unit based on the image data, the three-dimensional scanning data, or a combination thereof.

14. The x-ray system of claim 7, wherein the controller is further configured to carry out a check after carrying out a setting as to whether the examination object is changing a position, changing the setting, outputting a warning signal, or any combination thereof.

15. The x-ray system of claim 7, wherein the controller is further configured to carry out a first adjustment, in which the x-ray emission unit is aligned onto the examination object, prior to the acquisition of the image data.

\* \* \* \* \*